United States Patent [19]

Freed et al.

[11] Patent Number: 4,846,786
[45] Date of Patent: Jul. 11, 1989

[54] BIOREACTOR CONTAINING SUSPENDED, IMMOBILIZED SPECIES

[75] Inventors: Lisa E. Freed, Lincoln, Mass.; Jill R. C. Kadam, Vernon Hills, Ill.; Philip A. Drinker, Belmont, Mass.; J. Richard Thebeau, Wilmington, Mass.; Robert S. Langer, Somerville, Mass.

[73] Assignee: Massachusetts Institute of Technology, Cambridge, Mass.

[21] Appl. No.: 44,340

[22] Filed: Apr. 30, 1987

[51] Int. Cl.$^4$ ............................................ A61M 37/00
[52] U.S. Cl. ........................................ 604/4; 210/656; 530/413; 604/903
[58] Field of Search ........................... 604/4, 5, 6, 903; 210/198.2, 635, 656; 530/413, 417

[56] References Cited

U.S. PATENT DOCUMENTS

| | | | |
|---|---|---|---|
| 3,775,309 | 11/1973 | Ito et al. | 210/635 |
| 4,129,131 | 12/1978 | Naftulin | 604/903 |
| 4,215,688 | 8/1980 | Terman et al. | 604/5 |
| 4,243,532 | 1/1981 | Tsuda et al. | 210/196 |
| 4,359,389 | 11/1982 | Heine | 210/656 |
| 4,373,023 | 2/1983 | Langer et al. | 435/2 |
| 4,412,923 | 11/1983 | Capitani et al. | 210/661 |
| 4,490,290 | 12/1984 | Gani et al. | 260/112 B |
| 4,546,552 | 10/1985 | Cahn et al. | 210/656 |
| 4,740,313 | 4/1988 | Schoendorfer et al. | 210/651 |

FOREIGN PATENT DOCUMENTS

| | | |
|---|---|---|
| 2734741 | 2/1979 | Fed. Rep. of Germany ........... 604/5 |
| 3406562A1 | 8/1985 | Fed. Rep. of Germany . |

OTHER PUBLICATIONS

Drinker et al., Surgery 66:775–781 (1969).
Bartlett et al., Trans. Amer. Soc. Artif. Int. Organs, 18:369–374 (1972).
Bartlett et al., J. Thoracic Cardiovascular Surgery, 58(6):795–800 (1969).
Bernstein, et al., Kidney Int. 32:452–63 (1987a).
Larsen et al., Artif. Organs. 8:198–203 (1984a).
Langer et al., Science 217:261–263 (1982a).
Drinker et al., Artificial Lungs for Acute Respiratory Failure, Zapol, W. M. and Qvist, J. (eds) Academic Press, New York, pp. 69–86 (1976).
Bernstein, Methods in Enzymology, K. Mosback (ed.) Academic Press, New York, vol. 137, pp. 515–529 (1987c).
Bernstein et al., Biotech. & Bioeng. 30:239–250 (1987b).
Porath et al., J. Chromat., 60, 167 (1971).
Axen et al., Eur. J. Biochem., 18, 351 (1971).
March et al., Anal. Biochem., 60, 149 (1974).
Kohn et al., App. Biochem. and Biotech., 9 285 (1985).

(List continued on next page.)

Primary Examiner—C. Fred Rosenbaum
Assistant Examiner—Mario Costantino
Attorney, Agent, or Firm—Hamilton, Brook, Smith & Reynolds

[57] ABSTRACT

A reactor system especially suited for removal of chemical species from the bloodstream or other biological solutions containing suspended material. The reactor contains species such as enzymes, antibodies, receptors, anti-toxins, and a variety of drugs or inorganic compounds immobilized on particulate supports and/or solid phase adsorbents which react with specific materials under the appropriate conditions.

The reactor chamber is cylindrical and may optionally include a second cylinder internal to, and concentric with, the first cylinder, where the annular space between the pair of concentric cylinders forms the fluid path. The reactor chamber is oscillated through an arc of between approximately 50 and 90 degrees along an axis perpendicular to the axis of the flow of fluid through the reactor. The oscillatory motion in combination with the flow through the reactor maintains the particles in a fluidized state, preventing packing and maximizing reactivity.

The reactor as disclosed has a number of advantages over the prior art, including a more rapid flow rate and decreased incidence of cellular and immune-mediated blood damage.

19 Claims, 1 Drawing Sheet

OTHER PUBLICATIONS

Hearn et al., *J. Chromat.*, 185, 463 (1979).
Chapman et al., *Clinica Chimica Acta.*, 118, 129 (1982).
Bethel et al., *J. Chromat.*, 219, 353 (1981).
Bethel et al., *J. Chromat.* 219:361 (1981).
Sanderson et al., *Immunology*, 20, 1061 (1961).
Turkova et al., *Collection Czech. Chem. Commun.*, 44, 3411 (1979).
Linker et al., *Bioch.*, 11, 563 (1972).
Yin et al., *J. Lab. Clin. Med.*, 81, 298 (1973).
Estes, *Curr. Therapeut. Res.*, 18, 58 (1975).
Lam, *Biochem. Biophys. Res. Commun.*, 69, 570 (1976).
Jacques, *Pharmacol. Rev.*, 31, 89 (1980), pp. 99–166.
H. Bernstein, *Doctoral Thesis* (1985), "A System for Heparin Removal"–Title Page and Abstract.
Yang et al., "Removal of the Anticoagulant Activities . . . " (1986), Thromb. Res. 44(5), (pp. 599–610).
Bernstein et al., "Design of an Immobilized Enzyme Reactor" Polym. Mater. Sci. Eng. (1984) 51, pp. 204–207.
Begovich, J. M. et al.; "A Rotating Annular Chromatograph for Continuous Separations", AICHE Journal; vol. 30, No. 5; 9-1984; pp. 705–710.

BIOREACTOR CONTAINING SUSPENDED, IMMOBILIZED SPECIES

The United States has rights in this invention pursuant to National Institutes of Health Grant No. 5-RO1-GM25810-08.

BACKGROUND OF THE INVENTION

This invention is generally in the area of biological reactors and in particular is a method and apparatus for selective removal of chemical species from a biological fluid.

The removal of chemical species from the bloodstream using extracorporeal devices offers several advantages over conventional treatment modalities, such as transfusion therapy or the injection of a drug antagonist. In some instances, extracorporeal reactors may be the only therapy practical for toxins for which no antagonist is available.

Unfortunately, the complexity of the blood presents a number of problems. Mechanical damage to the cells can cause a low hematocrit or activation of the immune system. Damage to platelets can cause bleeding, a stroke or other clotting disorder. The high viscosity of blood and packing of the cells makes conventional filtration difficult due to blockage and nonspecific reactions or binding.

Extracorporeal reactors containing immobilized species have been constructed using three different types of solid phase configurations: particles, hollow fibers and planar sheets. Of these, particles provide the highest surface area per unit volume. The large surface area can potentially bind large quantities of various species which specifically react with the substances to be removed or treated in the blood.

At the present time, utilization of particles or "beads" for extracorporeal reactors is limited by packing of the solid phase in the device. This restricts the flow rates through the device to approximately 25 ml/min or less. Treatment of the entire blood volume of an adult patient, approximately 5,000 ml, through contact with the immobilized species within the device would require an impossible amount of time due to the risk and discomfort to the patient.

In order to use an extracorporeal reactor with particles or "beads" at clinically useful blood flow rates, a method of maintaining these beads in a suspended state is required. The desired flow rates are in the range of between approximately 50 ml/min to an excess of 1,000 ml/min. A second factor is that the device must be aprrovable by the Food and Drug Administration. All of the materials from which the unit is fabricated, as well as the unit as a whole, must be tested extensively before the device can be considered safe. Other considerations include a minimal priming volume, preferably not exceeding 300 ml, a means for preventing the "beads" from passing into the patient's bloodstream, and relatively easy assembly, cleaning, operation and modification, as required for the individual patient.

There are other applications of such a device for processing of biological solutions containing cellular materials or having a high viscosity. An example would be the removal of specific proteins expressed in a procaryotic expression system where conventional filtration causes cell death and release of degrading enzymes.

It is therefore an object of the present invention to provide a reactor chamber providing maximum surface area for reaction with a biological fluid, particularly cellular suspensions, such as blood or cell culture suspensions.

It is a further object of the present invention to provide a means to suspend and retain particles within the reactor chamber.

It is still a further object of the present invention to provide a reactor chamber having useful flow rates of from approximately 50 ml/min to an excess of 1,000 ml/min and a priming volume of less than approximately 300 ml.

It is another object of the present invention to provide a reactor chamber which is non-toxic, relatively easy to assemble and operate, and can meet FDA requirements.

SUMMARY OF THE INVENTION

A method and apparatus for selective removal of chemical species from biological fluids, especially blood and cell suspensions. The apparatus consists of a reactor chamber containing porous particles formed of a nonspecific, 'solid phase adsorbent or a polymer with immobilized reactive agents such as enzymes, antibodies, receptors, antitoxins, drugs and other organic and inorganic compounds.

In one embodiment of the apparatus, a cylindrical reactor chamber is provided containing cross-linked agarose beads to which an enzyme such as heparinase is bound, the beads or particles having diameters of between approximately 10 and 400 micrometers, the particles being restrained by a mesh having a pore size less than the particle diameter. In the preferred embodiment, the particles have diameters of about 200 micrometers and the pores in the restraining mesh are about 40 micrometers in diameter.

Optionally, the reactor chamber may be formed by inserting a second cylinder within and concentric to the primary cylindrical reactor chamber and passing fluid through the annular space between the pair of cylinders.

In either embodiment, the chamber is oscillated by an assembly consisting of a motor and connecting arm secured to the base of the cylindrical reactor vessel or other mechanical means. The torsional oscillation of the reactor vessel produces pairs of counter-rotating secondary flow cells which keep the beads evenly suspended within the reactor chamber, preventing them from either being propelled into the porous mesh across the outlet of the reactor chamber or settling to the bottom of the chamber. The maximum flow rate of blood through the device increases proportionately with increasing cross-sectional area of the outflow track. The volume is optimized to minimize pressure drop across the reactor.

BRIEF DESCRIPTION OF THE DRAWINGS

FIG. 1A showing the chamber prior to fluid flow therethrough; FIG. 1B showing the chamber in conjunction with a pump circulating fluid through the reactor chamber; and FIG. 1C showing the chamber with torsional oscillation of the circulating fluid.

DETAILED DESCRIPTION OF THE INVENTION

The present invention is a reactor especially suited for removal or treatment of substances in the bloodstream or other cell suspension. The primary advantage of the reactor is that it can maintain particulate materials having a high total surface area in a suspended state without packing at the outflow of the device even when the device is used in the treatment of solutions at high flow rates. Species such as enzymes, antibodies, receptors, anti-toxins, cofactors, carbohydrates, drugs, inorganic compounds, or combinations thereof, are immobilized on the particular supports and reacted with the solution to be treated. Alternatively, or in addition, nonspecific solid phase adsorbents can be placed in the reactor chamber to remove chemical species.

There are two presently preferred embodiments of the reactor chamber: a hollow cylinder and the annular space between a pair of concentric cylinders, one inside of the other. The reactor chamber is oscillated by means of an assembly such as a motor having a rotating eccentric drive attached via a connecting arm to the outer edge of one end of the reactor chamber. The drive is translated so that the reactor chamber moves through an arc of between approximately 50 and 90 degrees. The cross-sectional area of the reactor chamber is proportional to the desired flow rate and is most preferably optimized to minimize the pressure drop across the reactor.

Porous substrates or matrices within the reactor are used to maximize surface area available for reaction with the cell suspension. To maintain the particles in a suspended state, particles with diameters of between approximately 10 and 400 micrometers are selected for use in conjunction with a flow rate in the range of approximately 50 to 1,000 ml/min. The chamber is fitted at the outlet of the device with a restraining mesh having a pore size less than the particle diameter.

The general theory for operating the reactor is to shake the mixture of particles within the solution, while passing the solution through the reactor chamber, in such a manner as to form pairs of counterrotating flow cells within the chamber, thereby maintaining the particles in a suspended state even while fluid is flowing along an axis perpendicular to the axis of oscillation. The present invention avoids the mechanical and immune mediated damage caused by circulation of the fluid solution using mechanical means such as a peristatic roller pump.

The present invention is further described by reference to the appended drawings.

Figure 1A:
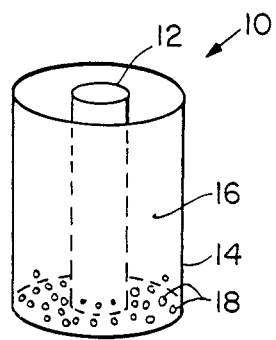
FIGS. 1A, 1B, and 1C are perspective views of a reactor chamber according to the present invention.
Figure 1B:
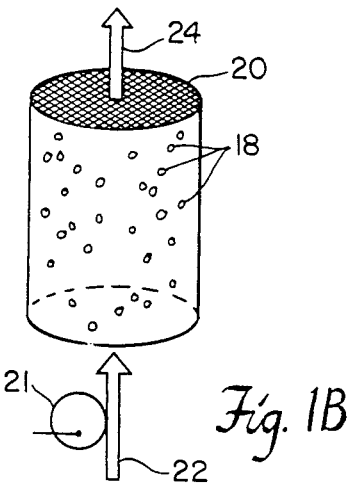
Figure 1C:
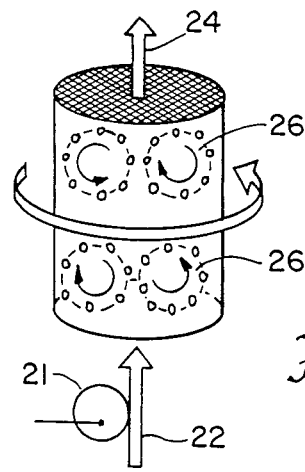

A reactor chamber 10 is shown in FIG. 1A. In one embodiment, the chamber 10 consists of a hollow cylinder 14. In a second embodiment, a second cylinder 12 is inserted within, and concentric to, the hollow cylinder 14, forming an annular gap 16 of uniform width. As shown in FIG. 1B, particles 18 are retained within the reactor by a restraining mesh 20 when the solution to be treated is pumped 21 through the reactor from the inlet 22 of the reactor chamber 10 to the outlet 24. The mesh 20 has pores of smaller diameter than the diameter of particles 18, for example, about 40 micrometers when crosslinked agarose particles having a diameter of about 200 micrometers are used. FIG. 1C diagrams the pairs of counterrotating secondary flow cells 26 produced by oscillating the chamber 10 while the solution is circulating through it. The effect of the flow cells 26 is to keep the particles 18 evenly suspended within the reactor chamber 10.

Figure 2:
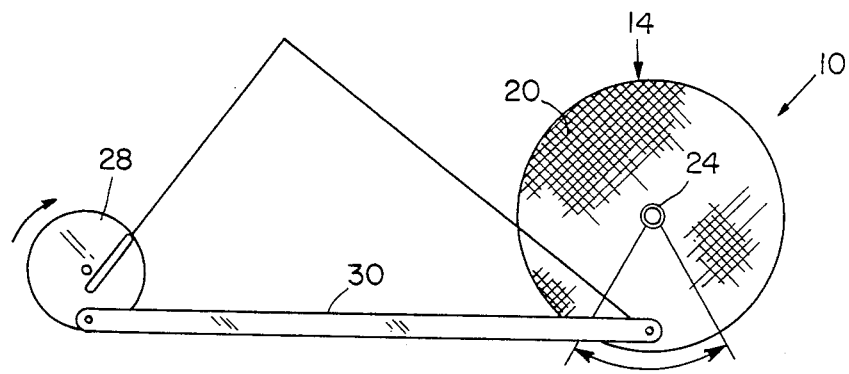
FIG. 2 is a plan view of the reactor chamber of FIG. 1 in combination with an oscillatory assembly according to the present invention.

One means for oscillation of the reactor chamber 10 about its axis is by a reciprocating connecting arm 30 connected to a rotating eccentric drive motor (300+ rpm) 28, as shown in FIG. 2. The arm 30 is connected to the base of the outer cylinder 14 of the reactor chamber 10 such that the reactor moves through an arc of between approximately 50° and 90°. This torsional oscillation produces the counterrotating secondary flow cells 26 which keep the particles 18 evenly suspended within the reactor chamber 10, preventing them from either being propelled into the mesh 20 (via the flow of blood through the device) or settling to the bottom via gravity. Other means for oscillating the reactor chamber in an equivalent manner could easily be substituted for this mechanism.

With the particles or beads suspended by the torsional oscillation of the reactor chamber, the maximal flow rate of blood through the device, $Q_{max}$ (ml/min), increases proportionally with increasing cross-sectional area of its outflow tract, A (cm$^2$): $Q_{max}=kA$. It has been empirically determined that if k is less than 8.5 cm/min, the pressure drop across the reactor is insignificant. "A" is either equal to $\pi R^2$ (for the first embodiment, the hollow cylinder) or the difference between the squares of the radii of the outer and inner cylinders, $R_{outer}$ and $R_{inner}$, respectively, where $A=\pi(R_{outer}^2 - R_{inner}^2)$ (for the second embodiment). "V", the priming volume of the device, $=AH$, where H is the height of the cylinder.

For example, for the first embodiment, given $R=4.5$ cm, then $A=63.6$ cm$^2$; $Q_{max}=540$ ml/min, $H=4.5$ cm and $V=285$ ml; or, for the second embodiment, given the specifications $R_{outer}=5.0$ cm, $R_{inner}=2.5$ cm, and $=5.5$ cm, then $A=59$ cm$^2$, $Q_{max}=500$ ml/min and $V=325$ ml.

The present invention is further described by the following non-limiting example.

An extracorporeal reactor for removing heparin from blood was constructed using the dimensions derived above for the first embodiment. This device is potentially useful in eliminating or decreasing the amount of heparin introduced into a patient undergoing an extracorporeal procedure such as membrane oxygenation or hemodialysis. The device contains 20 ml "wet volume" of cross-linked 8% agarose beads having 0.3-0.4 mg heparinase immobilized per ml of beads. The beads are restrained by a 33 micron mesh and fluidized by oscillating the reactor vessel about a 70° arc via an eccentric drive running at 350 rpm.

The reactor was tested both in vitro and ex vivo (in lambs) in an extracorporeal circuit. Efficacy studies were based on whole blood recalcification time measurements in blood sampled before and after passage through the reactor. Safety studies were based on serial monitoring of a number of parameters including complete blood cell count, platelet count, free plasma hemoglobin, and complement activation (CH50 and C3a). The results established that the reactor maintains the beads in a well suspended state while causing minimal hematological and immunological blood damage, allowing effective on-line neutralization of the heparin by the heparinase.

The present invention, an oscillating reactor system for treatment of biological solutions by reaction with compounds immobilized on suspended particles within the reactor, has been described with reference to specific embodiments. Other modifications and variations of the reactor system will be obvious to those skilled in the art. Such modifications and variations are intended to come within the scope of the appended claims.

What is claimed is:

1. An apparatus for the selective treatment of a biological fluid comprising:
   a reactor chamber;
   inlet means to the reactor chamber;
   outlet means from the reactor chamber;
   particulate material reacting with specific chemical species in the fluid, said material being contained within said chamber by retaining means; and
   oscillating means for moving said chamber circumferentially about the axis along which the fluid to be treated flows.

2. The apparatus of claim 1 wherein said reactor chamber is a hollow cylinder.

3. The apparatus of claim 1 wherein said reactor chamber is formed by the annular space between a first cylinder and a second cylinder, said first cylinder located within said second cylinder.

4. The apparatus of claim 1 wherein said oscillating means torsionally oscillates said reactor chamber at a rate proportional to the fluid flow rate through said chamber to produce counter-rotating secondary flow cells in said fluid, said flow cells maintaining said particulate material in suspension.

5. The apparatus of claim 1 wherein said particulate material comprises porous particles with diameters of between approximately 10 and 400 micrometers.

6. The apparatus of claim 1 wherein said material is selected from the group consisting of cellulose, agarose, polymethacrylate, polyurethane, polystyrene, and combinations thereof.

7. The apparatus of claim 5 wherein said retaining means is a restraining mesh having a pore size less than the particle diameters.

8. The apparatus of claim 1 wherein said particulate material includes a compound selected from the group consisting of enzymes, antibodies, receptors, anti-toxins, cofactors, drugs, dyes, carbohydrates and combinations thereof.

9. The apparatus of claim 8 wherein said compound is heparinase and said particulate material is crosslinked agarose beads.

10. A method for the selective treatment of a biological fluid, said method comprising:
    (a) providing fluid treatment apparatus which comprises:
       (i) a reactor chamber;
       (ii) means for forming an inlet to the reactor chamber;
       (iii) means for forming an outlet to the reactor chamber;
       (iv) particulate material for reacting with specific chemical species in the fluid, said material being contained within said chamber by retaining means; and
       (v) means for oscillating said chamber circumferentially about the axis along which the fluid to be treated flows; and
    (b) flowing said fluid to be treated through the fluid treatment apparatus while simultaneously oscillating the reaction chamber circumferentially about the axis along which the fluid to be treated flows, said oscillation producing counter-rotating secondary flow cells in said fluid to thereby maintain said particulate material in suspension.

11. The method of claim 10 wherein said reaction chamber comprises a hollow cylinder.

12. The method of claim 10 wherein said reaction chamber comprises an annular space between a first cylinder and a second cylinder, said first cylinder located within and concentric to said second cylinder.

13. The method of claim 10 wherein said particulate material comprises porous particles having diameters of between about 10 microns and about 400 microns, said particulate material having a biologically active material contained thereon.

14. The method of claim 13 wherein said particulate material is selected from the group consisting of cellulose, agarose, polymethacrylate, polyurethane, polystyrene and combinations thereof.

15. The method of claim 13 wherein said biologically active material comprises a compound selected from the group consisting of enzymes, antibodies, receptors, anti-toxins, cofactors, drugs, carbohydrates, dyes and combinations thereof.

16. The method of claim 15 wherein said biologically active material comprises heparinase.

17. The method of claim 16 wherein said fluid to be treated comprises heparinized blood.

18. The method of claim 17 wherein said fluid treatment apparatus is employed in an extracorporeal circuit for treatment of heparinized blood.

19. The method of claim 10 wherein said reaction chamber further contains material selected from the group consisting of ion exchangers and metal binding compounds.

* * * * *

UNITED STATES PATENT AND TRADEMARK OFFICE
CERTIFICATE OF CORRECTION

PATENT NO. : 4,846,786

DATED : July 11, 1989

INVENTOR(S) : Lisa E. Freed, Jill R.C. Kadam, Philip A. Drinker, J. Richard Thebeau and Robert S. Langer It is certified that error appears in the above-identified patent and that said Letters Patent is hereby corrected as shown below:

In Claim 1, line 4, delete "means" and insert -- --means for forming an-- -- before "inlet".

In Claim 1, line 5, delete "means" and insert -- --means for forming an-- -- before "outlet".

In Claim 1, line 6, insert -- --for-- -- after "material".

In Claim 1, line 9, delete "oscillating" and "moving" and insert -- --oscillating-- -- after "for".

Signed and Sealed this

Eighth Day of May, 1990

*Attest:*

HARRY F. MANBECK, JR.

*Attesting Officer*       *Commissioner of Patents and Trademarks*